(12) United States Patent
Kozakai et al.

(10) Patent No.: US 8,890,093 B2
(45) Date of Patent: Nov. 18, 2014

(54) CHARGED PARTICLE BEAM APPARATUS AND METHOD FOR FORMING OBSERVATION IMAGE

(71) Applicant: Hitachi High-Tech Science Corporation, Tokyo (JP)

(72) Inventors: Tomokazu Kozakai, Tokyo (JP); Fumio Aramaki, Tokyo (JP); Osamu Matsuda, Tokyo (JP)

(73) Assignee: Hitachi High-Tech Science Corporation (JP)

( * ) Notice: Subject to any disclaimer, the term of this patent is extended or adjusted under 35 U.S.C. 154(b) by 0 days.

(21) Appl. No.: 14/217,990

(22) Filed: Mar. 18, 2014

(65) Prior Publication Data

US 2014/0291509 A1    Oct. 2, 2014

(30) Foreign Application Priority Data

Mar. 26, 2013    (JP) .................................. 2013-063218

(51) Int. Cl.
| | |
|---|---|
| *H01J 37/30* | (2006.01) |
| *G01N 23/22* | (2006.01) |
| *H01J 3/14* | (2006.01) |
| *G01N 23/225* | (2006.01) |

(52) U.S. Cl.
CPC .................................. *G01N 23/2251* (2013.01)
USPC ...................... 250/492.1; 250/492.2; 250/310; 250/309; 250/307; 250/306; 250/397; 250/492.22

(58) Field of Classification Search
CPC ................. H01J 2237/2817; H01J 2237/2446; H01J 2237/244; H01J 37/21; H01J 2237/20221; H01J 37/261; G01N 23/225; G01N 23/2251
USPC .............. 250/310, 306, 307, 309, 397, 492.1, 250/492.2, 492.22
See application file for complete search history.

(56) References Cited

U.S. PATENT DOCUMENTS

| | | | |
|---|---|---|---|
| 7,138,629 B2* | 11/2006 | Noji et al. ...................... 250/311 |
| 7,485,880 B2* | 2/2009 | Kozakai et al. ........... 250/492.22 |
| 7,750,318 B2* | 7/2010 | Kozakai ..................... 250/492.1 |
| 2013/0228684 A1* | 9/2013 | Hatakeyama et al. ........ 250/310 |

FOREIGN PATENT DOCUMENTS

| | | |
|---|---|---|
| JP | 2009517840 | 4/2009 |
| WO | 2007067313 | 6/2007 |

* cited by examiner

*Primary Examiner* — Nikita Wells
(74) *Attorney, Agent, or Firm* — Adams & Wilks (57) ABSTRACT

A focused ion beam apparatus includes a lens interferometer configured to detect a relative position of an ion beam column and a sample. An image forming section includes an irradiation position specifying section configured to specify an irradiation position of an ion beam based on the detected relative position of the ion beam column and the sample, and a luminance setting section configured to set luminance of a pixel of an observation image based on the specified irradiation position of the ion beam and a detected amount of secondary particles.

6 Claims, 5 Drawing Sheets

*FIG. 6B* ered to form an observation image of the surface of the sample
CHARGED PARTICLE BEAM APPARATUS AND METHOD FOR FORMING OBSERVATION IMAGE This application claims priority from Japanese Patent Application No. 2013-063218 filed on Mar. 26, 2013, the entire subject-matter of which is incorporated herein by reference.

BACKGROUND

1. Technical Field

The present disclosure relates to a charged particle beam apparatus and a method for forming an observation image.

2. Description of Related Art

There has been known a focused ion beam apparatus for observing a surface of a sample such as a semiconductor device (for example, see JP-T-2009-517840). Generally, the focused ion beam apparatus includes an ion beam column that irradiates the surface of the sample with a focused ion beam, a detector that detects the amount of secondary electrons emitted from the surface of the sample by the irradiation of the ion beam, and an image forming section that forms an observation image of the surface of the sample based on the detected amount of the secondary electrons. The ion beam column sequentially irradiates the surface of the sample corresponding to a pixel of the observation image with the focused ion beam.

The image forming section forms the observation image of the sample based on a scanning signal output to the ion beam column and a detection signal input from the detector. The scanning signal represents a signal indicating the relationship between time and a pixel relating to irradiation of the ion beam, and the detection signal represents a signal indicating the relationship between time and the detected amount of the secondary electrons. The image forming section sets luminance corresponding to the amount of the secondary electrons for the pixel based on information about the pixel relating to irradiation of the ion beam at a specific time in the scanning signal and information about the amount of the secondary electrons detected at the specific time in the detection signal. In this way, by setting luminance for all pixels, the observation image is formed.

SUMMARY

The above-described formation of the observation image is performed on the assumption that a relative position of the ion beam column and the sample is not changed. However, the relative position of the ion beam column and the sample is changed, for example, by the influence of disturbance such as vibration of the apparatus. In this case, even though a specific pixel is intended to be irradiated with an ion beam at a specific time according to a scanning signal, a position different from the specific pixel may be irradiated with the ion beam. Thus, even though a luminance corresponding to the amount of secondary electrons detected at the specific time based on a detection signal is set for the specific pixel, a luminance that does not correspond to an actual state of a sample surface corresponding to the specific pixel may be set. In this way, when the relative position of the ion beam column and the sample is changed, it is difficult to form an accurate observation image.

Therefore, illustrative aspects of the invention provide a charged particle beam apparatus and a method for forming an observation image capable of forming an accurate observation image even when a relative position of a charged particle beam column and a sample is changed.

According to one illustrative aspect of the invention, there may be provided a charged particle beam apparatus comprising: a charged particle beam column configured to irradiate a surface of a sample with a charged particle beam; a detector configured to detect the amount of secondary particles emitted from the surface of the sample by the irradiation of the charged particle beam; and an image forming section configured to form an observation image of the surface of the sample based on the detected amount of the secondary particles, wherein the charged particle beam column is configured to irradiate the surface of the sample corresponding to a unit area of the observation image with the charged particle beam, wherein the charged particle beam apparatus further comprises a relative position detection unit configured to detect a relative position of the charged particle beam column and the sample, and wherein the image forming section is configured to: specify an irradiation position of the charged particle beam based on the detected relative position of the charged particle beam column and the sample; and set luminance of the unit area of the observation image based on the specified irradiation position of the charged particle beam and the detected amount of the secondary particles.

According to another illustrative aspect of the invention, there may be provided a method for forming an observation image, comprising: a charged particle beam irradiation process of irradiating a surface of a sample with a charged particle beam; a secondary particle amount detection process of detecting the amount of secondary particles emitted from the surface of the sample by the irradiation of the charged particle beam; and an image forming process of forming an observation image of the surface of the sample based on the detected amount of the secondary particles, wherein the charged particle beam irradiation process includes irradiating the surface of the sample corresponding to a unit area of the observation image with the charged particle beam, and wherein the image forming process comprises: detecting a relative position of the charged particle beam and the sample; specifying an irradiation position of the charged particle beam based on the detected relative position; and setting luminance of the unit area of the observation image based on the specified irradiation position of the charged particle beam and the detected amount of the secondary particles.

According to the above illustrative aspects, since the relative position of the charged particle beam column and the sample is detected, even when the relative position of the charged particle beam column and the sample is changed, it is possible to accurately specify an actual irradiation position of the charged particle beam. Further, since the luminance of the unit area of the observation image is set based on the specified irradiation position of the charged particle beam and the detected amount of secondary particles, even when a position different from the unit area that is an irradiation target is irradiated with the charged particle beam, it is possible to accurately set the luminance of the unit area of the observation image based on the actual irradiation position of the charged particle beam and the detected amount of secondary electrons. Accordingly, it is possible to form an accurate observation image.

In the above-described charged particle beam apparatus, it may be preferable that the image forming section is configured to: calculate an irradiation ratio to the unit area of the observation image from the specified irradiation position of the charged particle beam; allocate the amount of the secondary particles to the unit area of the observation image based on the calculated irradiation ratio and the detected amount of the secondary particles; and set the luminance of the unit area of the observation image based on the amount of the secondary particles allocated to the unit area of the observation image.

In the above-described method, it may be preferable that the image forming process further comprises: calculating an irradiation ratio to the unit area of the observation image from the specified irradiation position of the charged particle beam; allocating the amount of the secondary particles to the unit area of the observation image based on the calculated irradiation ratio and the detected amount of the secondary particles; and setting the luminance of the unit area of the observation image based on the amount of the secondary particles allocated to the unit area of the observation image.

According to the above illustrative aspects, since the irradiation ratio to the unit area of the observation image is calculated from the specified irradiation position of the charged particle beam, and the amount of secondary particles is allocated to the unit area of the observation image based on the calculated irradiation ratio and the detected amount of secondary particles, even when a position different from the unit area that is the irradiation target is irradiated with the charged particle beam, it is possible to accurately detect the amount of secondary particles emitted from the unit area of the observation image. Accordingly, it is possible to accurately set the luminance of the unit area of the observation image, to thereby form an accurate observation image.

In the above-described charged particle beam apparatus, it may be preferable that the image forming section is configured to set the luminance of the unit area of the observation image based on an average value of the amount of the secondary particles allocated to the unit area of the observation image.

In the above-described method, it may be preferable that the image forming process further comprises setting the luminance of the unit area of the observation image based on an average value of the amount of the secondary particles allocated to the unit area of the observation image.

According to the above illustrative aspects, since the luminance is set based on the average value of the amount of secondary particles allocated to the unit area of the observation image, even when the amount of secondary electrons due to the plural irradiations of the charged particle beam is allocated to the unit area, it is possible to accurately detect the amount of secondary electrons emitted from the unit area due to the single irradiation of the charged particle beam. Accordingly, it is possible to accurately set the luminance of the unit area of the observation image, to thereby form an accurate observation image.

According to the illustrative aspects, since the relative position of the charged particle beam column and the sample is detected, even when the relative position of the charged particle beam column and the sample is changed, it is possible to accurately specify an actual irradiation position of the charged particle beam. Further, since the luminance of the unit area of the observation image is set based on the specified irradiation position of the charged particle beam and the detected amount of secondary particles, even when a position different from the unit area that is an irradiation target is irradiated with the charged particle beam, it is possible to accurately set the luminance of the unit area of the observation image based on the actual irradiation position of the charged particle beam and the detected amount of secondary electrons. Accordingly, it is possible to form an accurate observation image.

BRIEF DESCRIPTION OF THE DRAWINGS

FIGS. 4A and 4B are diagrams illustrating an image forming operation when a relative position of an ion beam column 10 and a sample 2 is not changed, in which FIG. 4A shows an ion beam irradiation position, and FIG. 4B shows an image view of an observation image;

FIGS. 5A and 5B are graphs illustrating a position change of a sample stage 3, in which FIG. 5A shows a position change in an X direction, and FIG. 5B shows a position change in a Y direction; and FIGS. 6A and 6B are diagrams illustrating an image forming operation when a relative position of an ion beam column 10 and a sample 2 is changed, in which FIG. 6A shows an ion beam irradiation position, and FIG. 6B shows an image view of an observation image.

DETAILED DESCRIPTION

Hereinafter, as a charged particle beam apparatus, a focused ion beam apparatus provided with a gas field ionization ion source (GFIS) will be described as an example.

Figure 1:
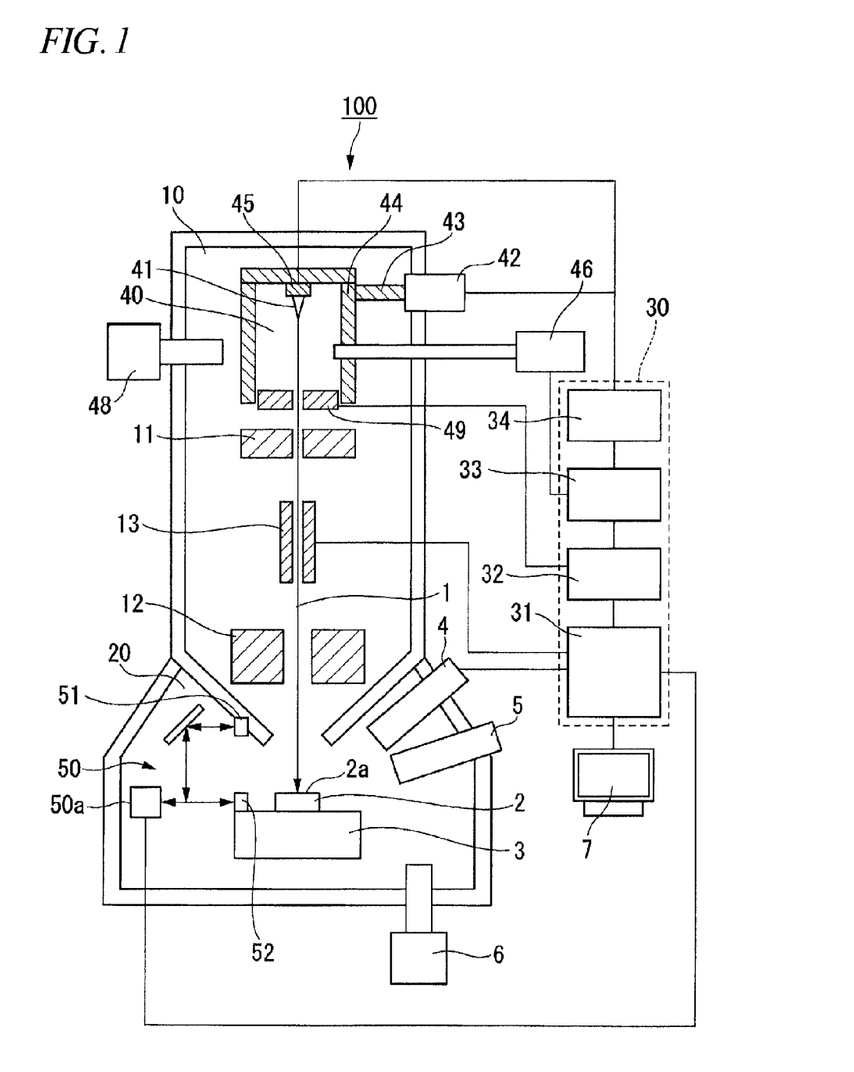
FIG. 1 is a configuration diagram of a focused ion beam apparatus 100 according to an illustrative embodiment of the invention.

FIG. 1 is a configuration diagram of a focused ion beam apparatus 100. The focused ion beam apparatus 100 includes an ion beam column 10 (charged particle beam column) that emits an ion beam (charged particle beam), a sample chamber 20 in which a sample 2 is disposed, and a control section 30 that controls respective components.

The ion beam column 10 includes an ion source chamber 40 that emits an ion beam 1, a condenser lens electrode 11 that condenses the ion beam 1, a deflector 13 that scans the ion beam 1 on a sample surface 2a, an objective lens electrode 12 that focuses the ion beam 1 on the sample surface 2a, and a vacuum pump 48 that evacuates the inside of the ion beam column 10.

The ion source chamber 40 is a gas field ionization ion source chamber, and is provided with an emitter 41 that emits the ion beam 1, an extraction electrode 49 disposed on a downstream side of the emitter 41, a wall section 44 that surrounds the emitter 41 in cooperation with the extraction electrode 49, an ion source gas supply section 46 that supplies an ion source gas to the ion source chamber 40, a cooling unit 42 that cools the ion source gas, and a heater 45 that adjusts the temperature of the emitter.

The emitter 41 is formed by coating a needle-like base material formed of tungsten (W) or molybdenum (Mo) with a precious metal such as platinum (Pt), palladium (Pd), indium (Ir), rhodium (Rh) or gold (Au). A tip of the emitter 41 is sharpened in a pyramid shape at an atomic level. The emitter 41 is fixed to a ceiling portion of the ion source chamber 40 through the heater 45.

The extraction electrode 49 applies a voltage between the emitter 41 and the extraction electrode 49 to ionize the ion source gas, and extracts the ion beam 1 from the ion source chamber 40.

The ion source gas supply section 46 supplies a gas such as hydrogen ($H_2$) or helium (He) to the ion source chamber 40, as the ion source gas.

The cooling unit 42 is connected to the wall section 44 through a connecting section 43. A coolant such as liquid nitrogen or liquid helium is accommodated inside the cooling unit 42. As the cooling unit 42, a closed cyclic freezer of a GM type, a pulse tube type or the like, or a gas flow type freezer may be used.

An operation of the ion source chamber 40 will be described.

The ion source gas is supplied into the ion source chamber 40 from the ion source gas supply section 46, and is cooled by the cooling unit 42. Thus, a high-density ion source gas is disposed around the emitter 41. Then, a voltage is applied between the emitter 41 and the extraction electrode 49 by the extraction electrode 49. Since the tip of the emitter 41 is sharpened at the atomic level, an extremely large electric field is formed at the tip of the emitter 41, and thus, the ion source gas is ionized. Further, by applying a voltage between the emitter 41 and the extraction electrode 49 by the extraction electrode 49, the ion beam 1 is extracted from the ion source chamber 40. By extracting the ion beam 1 from the tip of the emitter 41 sharpened at the atomic level, the ion beam 1 having a micro beam diameter is emitted. The sample surface 2a is irradiated with the ion beam 1 emitted from the ion source chamber 40.

The sample chamber 20 is provided with a sample stage 3 on which the sample 2 is mounted, a detector 4 that detects the amount of secondary electrons emitted from the sample surface 2a by the irradiation of the ion beam 1, a gas supply section 5 that applies a gas to the sample surface 2a, and a vacuum pump 6 that evacuates the inside of the sample chamber 20.

The sample stage 3 controls the position and posture of the mounted sample 2. To this end, the sample stage 3 includes a movement mechanism for movement in an XY axis direction in a horizontal plane and in a Z axis direction perpendicular to the horizontal plane, a tilt mechanism for inclination around the XY axis, and a rotation mechanism for rotation around the Z axis.

The detector 4 detects the amount of secondary electrons as the amount of secondary particles, but may detect the amount of secondary ions. The detector 4 outputs the amount of secondary electrons detected in a unit time to the control section 30.

The gas supply section 5 applies the gas to the sample surface 2a during the irradiation of the ion beam 1. According to the type of applied gas, it is possible to perform etching of the sample surface 2a or deposition to the sample surface 2a.

The control section 30 includes a temperature control section 34 that controls operations of the cooling unit 42 and the heater 45 of the ion source chamber 40, an ion source gas control section 33 that controls an operation of the ion source gas supply section 46, an extraction voltage control section 32 that controls a voltage applied to the extraction electrode 49, the image forming section 31 that forms an observation image of the sample surface 2a, and a display section 7 that displays the formed observation image.

(Image Forming Section)

The same signal as a scanning signal (a signal for scanning the sample surface 2a with the ion beam) input to the deflector 13 is input to the image forming section 31. Further, a detection signal of the amount of secondary electrons is input to the image forming section 31 from the detector 4. Further, the image forming section 31 forms the observation image of the sample surface 2a, based on the scanning signal and the detection signal.

Figure 4A:
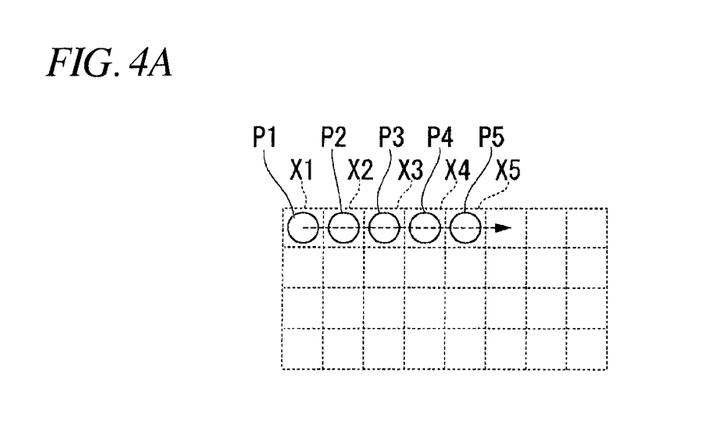
Figure 4B:
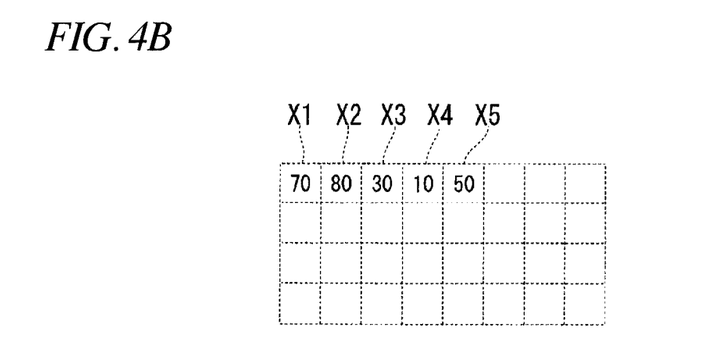

FIGS. 4A and 4B are diagrams illustrating an image forming operation when a relative position of the ion beam column 10 and the sample 2 is not changed, in which FIG. 4A shows an ion beam irradiation position, and FIG. 4B is an image diagram of an observation image (in which luminance is expressed by numerical values). As shown in FIG. 4A, an area where the observation image is formed on the sample surface 2a is divided into latticed pixels X. The formation area of the observation image may be divided into unit areas other than the pixels. Further, the image forming section 31 receives the same signal as the scanning signal input to the deflector 13. The scanning signal is a signal for sequentially irradiating the sample surface 2a corresponding to each pixel X with an ion beam P. The irradiation of the ion beam P is performed to remain on the sample surface corresponding to each pixel X for a predetermined time (for example, 10 μsec). In the example in FIGS. 4A and 4B, since the relative position of the ion beam column 10 and the sample 2 is not changed, an irradiation position of an ion beam P1 at time T1 is specified to (the sample surface corresponding to) a pixel X1. Similarly, an irradiation position (of an ion beam P2) at time T2 is specified to a pixel X2, an irradiation position (of an ion beam P3) at time T3 is specified to a pixel X3, an irradiation position (of an ion beam P4) at time T4 is specified to a pixel X4, and an irradiation position (of an ion beam P5) at time T5 is specified to a pixel X5, respectively.

Figure 3:
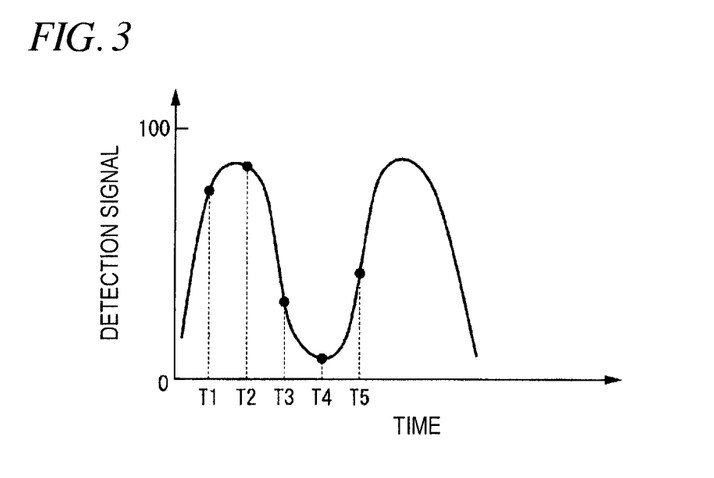
FIG. 3 is a graph of a detection signal of the amount of secondary electrons.

FIG. 3 is a graph illustrating a detection signal of the amount of secondary electrons. The detector 4 detects the amount of secondary electrons emitted from the sample surface 2a by the irradiation of the ion beam, and outputs the detection signal to the image forming section 31. In the example of the detection signal shown in FIG. 3, the amount of secondary electrons of 70 points is detected at time T1. Similarly, the amount of secondary electrons of 80 points is detected at time T2, the amount of secondary electrons of 30 points is detected at time T3, the amount of secondary electrons of 10 points is detected at time T4, and the amount of secondary electrons of 50 points is detected at time T5, respectively.

The image forming section 31 forms the observation image of the sample surface 2a based on the scanning signal and the detection signal. That is, the observation image of the sample surface 2a is formed by the irradiation position of the ion beam specified based on the scanning signal and the amount of secondary electrons included in the detection signal. In the example shown in FIG. 4A and FIG. 3, the amount of secondary electrons of 70 points is detected by the irradiation of the ion beam P1 to the pixel X1. Thus, as shown in FIG. 4B, a luminance corresponding to 70 points is set for the pixel X1. Similarly, a luminance corresponding to 80 points is set for the pixel X2, a luminance corresponding to 30 points is set for the pixel X3, a luminance corresponding to 10 points is set for the pixel X4, and a luminance corresponding to 50 points is set for the pixel X5, respectively. In this way, the entirety of the observation image is formed.

(Image Forming Operation when Relative Position is Changed)

Figure 6A:
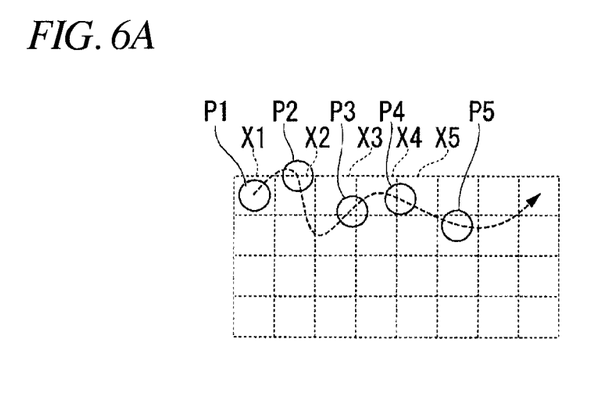
Figure 6B:
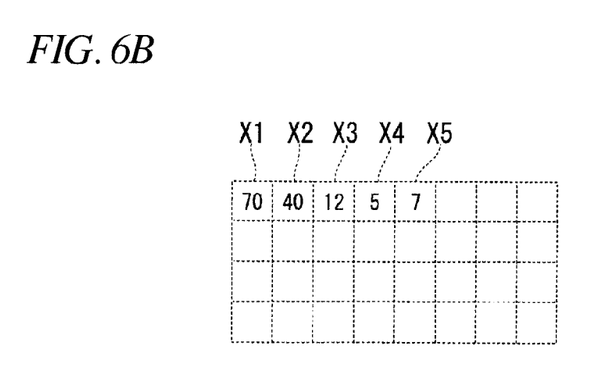

FIGS. 6A and 6B are diagrams illustrating an image forming operation when the relative position of the ion beam column 10 and the sample 2 is changed, in which FIG. 6A shows an ion beam irradiation position, and FIG. 6B is an image diagram of an observation image (in which luminance is expressed by numerical values). The above-described formation of the observation image is performed on the assumption that the relative position of the ion beam column 10 and the sample 2 is not changed. However, the relative position of the ion beam column 10 and the sample 2 is changed, for example, by the influence of disturbance such as vibration or the like of the focused ion beam apparatus 100. In this case, an irradiation track of the ion beam becomes irregular as shown in FIG. 6A. Thus, even though the sample surface 2a corresponding to the pixel X2 is intended to be irradiated with the ion beam P2 according to the scanning signal, in reality, a position different from the pixel X2 is irradiated with the ion beam P2. Similarly, positions different from the pixels X3 to X5 are irradiated with the ion beams P3 to P5.

Thus, in the present illustrative embodiment, even though the relative position of the ion beam column 10 and the sample 2 is changed, an actual irradiation position of an ion beam is specified, to thereby form an accurate observation image.

Specifically, a relative position detection process of detecting the relative position of the ion beam column 10 and the sample 2, an irradiation position specification process of specifying the irradiation position of the ion beam based on the detected relative position, and a luminance setting process of setting the luminance of the pixel of the observation image based on the irradiation position of the specified ion beam and the amount of secondary electrons are performed. In the luminance setting process, a luminance ratio calculation process of calculating an irradiation ratio to each pixel from the specified irradiation position of the ion beam and a secondary electron amount allocation process of allocating the amount of secondary electrons to each pixel based on the calculated irradiation ratio and the detected amount of the secondary electrons are performed, and then, the luminance of each pixel is set based on the allocated amount of secondary electrons and the observation image is formed.

First, the relative position of the ion beam column 10 and the sample 2 is detected (the relative position detection process).

As shown in FIG. 1, in the sample chamber 20, a laser interferometer 50 is provided as means for detecting the relative position of the ion beam column 10 and the sample 2. The laser interferometer 50 is arranged in the X direction and the Y direction in the horizontal plane, respectively. The laser interferometer 50 includes a laser irradiation device 50a, a column side reflecting surface 51 fixed to the ion beam column 10, and a sample side reflecting surface 52 fixed to the sample stage 3. The laser interferometer 50 irradiates the column side reflecting surface 51 and the sample side reflecting surface 52 with laser from the laser irradiation device 50a, measures displacement of the ion beam column 10 and the sample stage 3, and outputs the measurement result to the image forming section 31.

Figure 5A:
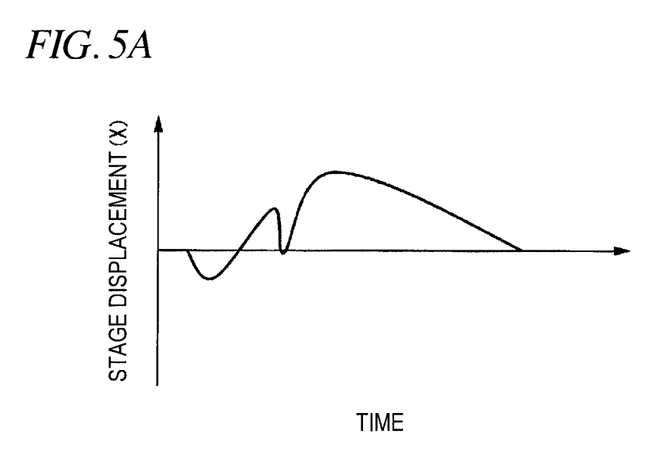
Figure 5B:
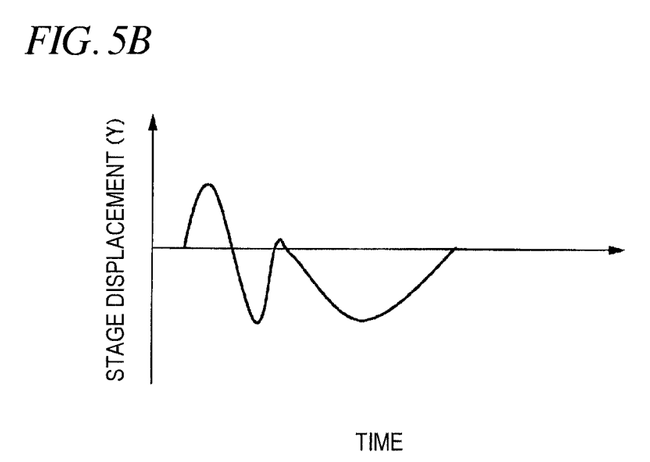

FIGS. 5A and 5B are graphs illustrating displacement (shift amount) of the sample stage 3, in which FIG. 5A shows the displacement in the X direction, and FIG. 5B shows the displacement in the Y direction. The displacement of the sample stage 3 is measured by the above-described laser interferometer 50, as shown in FIGS. 5A and 5B. It is possible to detect the displacement of the sample 2 mounted on the sample stage 3 from the measurement result of the displacement of the sample stage 3.

In this way, by detecting the displacement of the ion beam column 10 and the displacement of the sample 2 with reference to the laser irradiation device 50a, it is possible to detect the relative position of the ion beam column 10 and the sample 2.

Next, the irradiation position of the ion beam is specified based on the detected relative position (irradiation position specification process).

Figure 2:
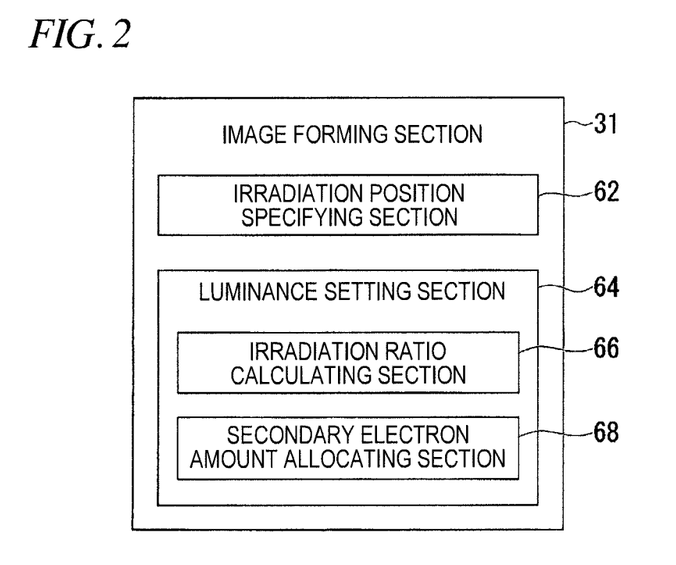
FIG. 2 is a configuration diagram of an image forming section 31.

FIG. 2 is a configuration diagram of the image forming section 31. The image forming section 31 includes an irradiation position specifying section 62 that specifies the irradiation position of the ion beam based on the detected relative position of the ion beam column 10 and the sample 2.

In the example shown in FIG. 6A, the ion beam P2 that is intended to irradiate the sample surface 2a corresponding to the pixel X2 at the specific time T2 irradiates a position different from the pixel X2. Thus, the irradiation position specifying section 62 of the image forming section 31 specifies an actual irradiation position of the ion beam on the sample surface 2a at the specific time T2 by adding the relative position information of the ion beam column 10 and the sample 2 at the specific time T2 to position information about the sample surface 2a corresponding to the pixel X2.

Next, the luminance of the pixel of the observation image is set based on the specified irradiation position of the ion beam and the amount of secondary electrons (luminance setting process). As shown in FIG. 2, the image forming section 31 includes a luminance setting section 64 that sets the luminance of the pixel of the observation image based on the specified irradiation position of the ion beam and the detected amount of secondary electrons.

In the luminance setting process, an irradiation ratio to each pixel is calculated from the specified irradiation position of the ion beam (irradiation ratio calculation process), and the amount of secondary electrons is allocated to each pixel based on the calculated irradiation ratio and the detected amount of secondary electrons (secondary electron amount allocation process). Further, the luminance of each pixel is set based on an average value of the amount of secondary electrons allocated to each pixel.

As shown in FIG. 2, the luminance setting section 64 includes an irradiation ratio calculating section 66, and a secondary electron amount allocating section (secondary particle amount allocating section) 68. The irradiation ratio calculating section 66 calculates the irradiation ratio to each pixel from the specified irradiation position of the ion beam. The secondary electron amount allocating section 68 allocates the amount of secondary electrons to each pixel based on the calculated irradiation ratio and the detected amount of secondary electrons. Further, the luminance setting section 64 sets the luminance of each pixel based on the average value of the amount of secondary electrons allocated to each pixel.

In the example shown in FIG. 6A, the entirety of the ion beam P2 does not irradiate the pixel X2, but since a part of the ion beam P2 irradiates the pixel X2, the secondary electrons are also emitted from the pixel X2 in addition to other pixels. The ratio of the amount of secondary electrons emitted from the pixel X2 in the amount of secondary electrons detected by the detector 4 corresponds to the irradiation ratio of the ion beam P2 to the pixel X2. Thus, the luminance setting section 64 calculates the irradiation ratio to each pixel from the irradiation position of the ion beam. Then, the secondary electron amount allocating section 68 multiplies the detected amount of secondary electrons by the irradiation ratio to each pixel to allocate the amount of secondary electrons to each pixel. After allocating the amount of secondary electrons detected for the entirety of the ion beams to each pixel, the luminance setting section 64 calculates the average value of the amount of secondary electrons allocated to each pixel. Further, the luminance setting section 64 sets the luminance of each pixel based on the average value of the calculated amount of secondary electrons, as shown in FIG. 6B.

The examples shown in FIGS. 6A and 6B will be specifically described. First, the irradiation ratio of the ion beam P1 to the pixel X1 is calculated as 100% from the irradiation position of the ion beam P1 at time T1. Further, in the detection signal shown in FIG. 3, the amount of secondary electrons detected at time T1 corresponds to 70 points. Thus, the amount of secondary electrons of 70 points is multiplied by 100/100 of the irradiation ratio to the pixel X1, and the amount of secondary electrons of 70 points is allocated to the pixel X1. Since the amount of secondary electrons allocated to the pixel X1 is only 70 points at time T1, the average value of the amount of secondary electrons allocated to the pixel X1 is 70 points. Thus, as shown in FIG. 6B, the luminance corresponding to 70 points is set for the pixel X1.

Further, the irradiation ratio of the ion beam P2 to the pixel X2 is calculated as 50% from the irradiation position of the ion beam P2 at time T2. The amount of secondary electrons of 80 points detected at time T2 is multiplied by 50/100 of the irradiation ratio to the pixel X2, and the amount of secondary electrons of 40 points is allocated to the pixel X2. Since the average value of the amount of secondary electrons allocated to the pixel X2 is 40 points, the luminance corresponding to 40 points is set for the pixel X2.

Further, the irradiation ratio of the ion beam P3 to the pixel X3 is calculated as 40% from the irradiation position of the ion beam P3 at time T3. The amount of secondary electrons of 30 points detected at time T3 is multiplied by 40/100 of the irradiation ratio to the pixel X3, and the amount of secondary electrons of 12 points is allocated to the pixel X3. Since the average value of the amount of secondary electrons allocated to the pixel X3 is 12 points, the luminance corresponding to 12 points is set for the pixel X3.

The ion beam P3 irradiates both of the pixel X3 and the pixel X4. The irradiation ratio of the ion beam P3 to the pixel X4 is calculated as 25% from the irradiation position of the ion beam P3 at time T3. The amount of secondary electrons of 30 points detected at time T3 is multiplied by 25/100 of the irradiation ratio to the pixel X4, and the amount of secondary electrons of 7.5 points is allocated to the pixel X4.

On the other hand, the irradiation ratio of the ion beam P4 to the pixel X4 is calculated as 30% from the irradiation position of the ion beam P4 at time T4. The amount of secondary electrons of 10 points detected at time T4 is multiplied by 30/100 of the irradiation ratio to the pixel X4, and the amount of secondary electrons of 3 points is allocated to the pixel X4.

In this way, since the amounts of secondary electrons of 7.5 points at time T3 and 3 points at time T4 are allocated to the pixel X4, the average value of the amount of secondary electrons allocated to the pixel X4 is about 5 points. Thus, the luminance corresponding to 5 points is set for the pixel X4.

Further, the irradiation ratio of the ion beam P4 to the pixel X5 is calculated as 70% from the irradiation position of the ion beam P4 at time T4. The amount of secondary electrons of 10 points detected at time T4 is multiplied by 70/100 of the irradiation ratio to the pixel X4, and the amount of secondary electrons of 7 points is allocated to the pixel X5.

On the other hand, the irradiation ratio of the ion beam P5 to the pixel X5 is calculated as 0% from the irradiation position of the ion beam P5 at time T5. Thus, the allocation of the amount of secondary electrons to the pixel X5 at time T5 is not performed.

Accordingly, the average value of the amount of secondary electrons allocated to the pixel X5 is 7 points, and thus, the luminance corresponding to 7 points is set for the pixel X5.

Similarly, the luminance of all pixels is set to thereby form the observation image. In the present illustrative embodiment, the irradiation time of all ion beams is constant, but the irradiation time may be changed for each ion beam. In this case, it is preferable that the detected amount of secondary electrons be divided by the ion beam irradiation time to evaluate the amount of secondary electrons in a unit irradiation time.

As described above, the focused ion beam apparatus 100 of the present illustrative embodiment has a configuration in which the laser interferometer 50 that detects the relative position of the ion beam column 10 and the sample 2 is provided and the image forming section 31 includes the irradiation position specifying section 62 that specifies the irradiation position of the ion beam based on the detected relative position of the ion beam column 10 and the sample 2 and the luminance setting section 64 that sets the luminance of the pixel of the observation image based on the specified irradiation position of the ion beam and the detected amount of secondary electrons.

According to this configuration, since the relative position of the ion beam column 10 and the sample 2 is detected, even when the relative position of the ion beam column 10 and the sample 2 is changed, it is possible to accurately specify the actual irradiation position of the ion beam. Further, since the luminance of the pixel of the observation image is set based on the specified irradiation position of the ion beam and the detected amount of secondary electrons, even when a position different from a pixel that is an irradiation target is irradiated with the ion beam, it is possible to accurately set the luminance of the pixel of the observation image based on the actual irradiation position of the ion beam and the detected amount of secondary electrons. Accordingly, it is possible to form an accurate observation image.

Further, the luminance setting section 64 is configured to include the irradiation ratio calculating section 66 that calculates the irradiation ratio to the pixel of the observation image from the specified irradiation position of the ion beam and the secondary electron amount allocating section 68 that allocates the amount of secondary electrons to the pixel of the observation image based on the calculated irradiation ratio and the detected amount of secondary electrons, and is configured to set the luminance of the pixel of the observation image based on the amount of secondary electrons allocated to the pixel of the observation image.

According to this configuration, since the irradiation ratio to the pixel of the observation image is calculated from the specified irradiation position of the ion beam and the amount of secondary electrons is allocated to the pixel of the observation image based on the calculated irradiation ratio and the detected amount of secondary electrons, even when the position different from the pixel that is the irradiation target is irradiated with the ion beam, it is possible to accurately detect the amount of secondary electrons emitted from the pixel of the observation image. Accordingly, it is possible to accurately set the luminance of the pixel of the observation image, to thereby form an accurate observation image.

Further, the luminance setting section is configured to set the luminance of the pixel of the observation image based on the average value of the amount of secondary electrons allocated to the pixel of the observation image.

According to the configuration, since the luminance is set based on the average value of the amount of secondary electrons allocated to the pixel, even when the amount of the secondary electrons due to the plural irradiations of the ion beam is allocated to the pixel, it is possible to accurately detect the amount of secondary electrons emitted from the pixel due to the single irradiation of the ion beam. Accordingly, it is possible to accurately set the luminance of the pixel of the observation image, to thereby form an accurate observation image.

The technical scope of the invention is not limited to the above-described illustrative embodiments, and includes various modifications of the illustrative embodiments in a range without departing from the spirit of the invention. That is, the specific materials, layer configurations and the like shown in the illustrative embodiments are only an example, and may be appropriately modified.

For example, in the above-described illustrative embodiments, the focused ion beam apparatus provided with the gas field ionization ion source (GFIS) is described as the charged particle beam apparatus as an example, but a focused ion beam apparatus provided with a different ion source such as a plasma ion source or a liquid metal ion source may be employed. Further, an electronic beam apparatus that emits an electronic beam may be employed as the charged particle beam apparatus.

What is claimed is:

1. A charged particle beam apparatus comprising:
a charged particle beam column configured to irradiate a surface of a sample with a charged particle beam;
a detector configured to detect the amount of secondary particles emitted from the surface of the sample by the irradiation of the charged particle beam; and
an image forming section configured to form an observation image of the surface of the sample based on the detected amount of the secondary particles,
wherein the charged particle beam column is configured to irradiate the surface of the sample corresponding to a unit area of the observation image with the charged particle beam,
wherein the charged particle beam apparatus further comprises a relative position detection unit configured to detect a relative position of the charged particle beam column and the sample, and
wherein the image forming section is configured to:
specify an irradiation position of the charged particle beam based on the detected relative position of the charged particle beam column and the sample; and
set luminance of the unit area of the observation image based on the specified irradiation position of the charged particle beam and the detected amount of the secondary particles.

2. The charged particle beam apparatus according to claim 1, wherein the image forming section is configured to:
calculate an irradiation ratio to the unit area of the observation image from the specified irradiation position of the charged particle beam;
allocate the amount of the secondary particles to the unit area of the observation image based on the calculated irradiation ratio and the detected amount of the secondary particles; and
set the luminance of the unit area of the observation image based on the amount of the secondary particles allocated to the unit area of the observation image.

3. The charged particle beam apparatus according to claim 2, wherein the image forming section is configured to set the luminance of the unit area of the observation image based on an average value of the amount of the secondary particles allocated to the unit area of the observation image.

4. A method for forming an observation image, comprising:
a charged particle beam irradiation process of irradiating a surface of a sample with a charged particle beam;
a secondary particle amount detection process of detecting the amount of secondary particles emitted from the surface of the sample by the irradiation of the charged particle beam; and
an image forming process of forming an observation image of the surface of the sample based on the detected amount of the secondary particles,
wherein the charged particle beam irradiation process includes irradiating the surface of the sample corresponding to a unit area of the observation image with the charged particle beam, and
wherein the image forming process comprises:
detecting a relative position of the charged particle beam and the sample;
specifying an irradiation position of the charged particle beam based on the detected relative position; and
setting luminance of the unit area of the observation image based on the specified irradiation position of the charged particle beam and the detected amount of the secondary particles.

5. The method for forming the observation image according to claim 4, wherein the image forming process further comprises:
calculating an irradiation ratio to the unit area of the observation image from the specified irradiation position of the charged particle beam;
allocating the amount of the secondary particles to the unit area of the observation image based on the calculated irradiation ratio and the detected amount of the secondary particles; and
setting the luminance of the unit area of the observation image based on the amount of the secondary particles allocated to the unit area of the observation image.

6. The method for forming the observation image according to claim 5, wherein the image forming process further comprises setting the luminance of the unit area of the observation image based on an average value of the amount of the secondary particles allocated to the unit area of the observation image.

* * * * *